(12) United States Patent
Seymour et al.

(10) Patent No.: US 9,700,736 B2
(45) Date of Patent: Jul. 11, 2017

(54) NEUROMODULATION TRANSFECTION SYSTEM WITH ACTIVE FLUID DELIVERY

(75) Inventors: John P. Seymour, Ann Arbor, MI (US); Kc Kong, Ann Arbor, MI (US); Rio J. Vetter, Ypsilanti, MI (US)

(73) Assignee: NEURONEXUS TECHNOLOGIES, INC., Ann Arbor, TX (US)

( * ) Notice: Subject to any disclaimer, the term of this patent is extended or adjusted under 35 U.S.C. 154(b) by 1386 days.

(21) Appl. No.: 13/557,536

(22) Filed: Jul. 25, 2012

(65) Prior Publication Data
US 2013/0030352 A1 Jan. 31, 2013

Related U.S. Application Data

(60) Provisional application No. 61/511,371, filed on Jul. 25, 2011.

(51) Int. Cl.
| | |
|---|---|
| *A61N 5/06* | (2006.01) |
| *A61B 5/04* | (2006.01) |
| *A61N 1/32* | (2006.01) |
| *A61N 1/05* | (2006.01) |

(Continued)

(52) U.S. Cl.
CPC ........ *A61N 5/0622* (2013.01); *A61B 5/04001* (2013.01); *A61N 1/0551* (2013.01); *A61N 1/327* (2013.01); *A61B 5/4839* (2013.01); *A61B 5/6868* (2013.01); *A61B 2562/0209* (2013.01); *A61B 2562/046* (2013.01); *A61N 1/0529* (2013.01); *A61N 2005/063* (2013.01); *A61N 2005/067* (2013.01); *A61N 2005/0612* (2013.01); *A61N 2005/0651* (2013.01)

(58) Field of Classification Search
CPC ................ A61N 1/0551; A61N 1/0534; A61N 1/36071; A61N 1/0529; A61N 1/36082; A61N 1/0539; A61N 1/3605; A61N 1/0531; A61N 1/0556; A61N 1/04; A61B 5/6868
USPC ........ 600/372–373, 377–378, 393, 544–545; 607/115–118
See application file for complete search history.

(56) References Cited

U.S. PATENT DOCUMENTS

| | | |
|---|---|---|
| 3,628,017 A | 12/1971 | Lerner |
| 5,629,009 A | 5/1997 | Laurencin et al. |
| 6,238,994 B1 | 5/2001 | Derderian et al. |

(Continued)

FOREIGN PATENT DOCUMENTS

| | | |
|---|---|---|
| WO | 2008/089003 | 7/2008 |
| WO | 2009/072123 | 6/2009 |

(Continued)

OTHER PUBLICATIONS

"International Preliminary Report on Patentability", PCT/US2012/048075, Jan. 28, 2014.

(Continued)

*Primary Examiner* — Joseph Stoklosa
*Assistant Examiner* — Brian M Antiskay
(74) *Attorney, Agent, or Firm* — Haynes and Boone, LLP; Taylor Merritt Meacham

(57) ABSTRACT

A neural interface array including an optical waveguide, a thin film electrode array associated with the optical waveguide, the thin film electrode array having a plurality of electrodes, and a fluid delivery channel attached to at least one of the optical waveguide and the thin film electrode array. Also disclosed are methods for optical stimulation and a neural interface system with active fluid delivery.

24 Claims, 4 Drawing Sheets

(51) Int. Cl.
  *A61N 5/067* (2006.01)
  *A61B 5/00* (2006.01)

(56) References Cited

U.S. PATENT DOCUMENTS

| | | | |
|---|---|---|---|
| 6,294,074 B1 | 9/2001 | Lin et al. | |
| 6,819,958 B2* | 11/2004 | Weiner | A61N 1/056 600/372 |
| 7,096,070 B1* | 8/2006 | Jenkins | A61N 1/05 128/898 |
| 7,116,886 B2* | 10/2006 | Colgan | G02B 6/3636 385/137 |
| 7,310,546 B2 | 12/2007 | Prass | |
| 7,375,870 B2 | 5/2008 | Schorpp | |
| 7,781,195 B1 | 8/2010 | Heller et al. | |
| 7,955,889 B1 | 6/2011 | Yang et al. | |
| 8,005,526 B2 | 8/2011 | Martin et al. | |
| 8,986,292 B2* | 3/2015 | Sliwa | A61B 5/0084 606/15 |
| 2002/0183682 A1 | 12/2002 | Darvish et al. | |
| 2003/0091289 A1* | 5/2003 | Saito | G02B 6/12009 385/49 |
| 2003/0147958 A1 | 8/2003 | Ahn et al. | |
| 2004/0111139 A1 | 6/2004 | McCreery | |
| 2006/0024359 A1 | 2/2006 | Walker et al. | |
| 2009/0024195 A1* | 1/2009 | Rezai | A61N 1/36007 607/116 |
| 2009/0054954 A1 | 2/2009 | Foley et al. | |
| 2009/0099038 A1 | 4/2009 | Deisseroth et al. | |
| 2009/0118800 A1 | 5/2009 | Deisseroth et al. | |
| 2009/0210039 A1* | 8/2009 | Boyden | A61N 5/0618 607/89 |
| 2009/0292325 A1 | 11/2009 | Cederna et al. | |
| 2010/0015095 A1 | 1/2010 | Pan et al. | |
| 2010/0049263 A1 | 2/2010 | Reeve | |
| 2010/0161017 A1 | 6/2010 | Choi et al. | |
| 2010/0190229 A1 | 7/2010 | Zhang et al. | |
| 2010/0191308 A1 | 7/2010 | Meister | |
| 2010/0211172 A1 | 8/2010 | Bellamkonda et al. | |
| 2010/0268150 A1 | 10/2010 | Mohanty et al. | |
| 2011/0021970 A1 | 1/2011 | Vo-Dinh et al. | |
| 2011/0087126 A1 | 4/2011 | Zorzos et al. | |
| 2011/0093052 A1 | 4/2011 | Anderson et al. | |
| 2011/0105998 A1 | 5/2011 | Zhang et al. | |
| 2011/0112591 A1 | 5/2011 | Seymour et al. | |
| 2011/0144566 A1 | 6/2011 | Dacey, Jr. et al. | |
| 2011/0172736 A1 | 7/2011 | Gefen et al. | |
| 2011/0295347 A1* | 12/2011 | Wells | A61N 1/36032 607/89 |
| 2011/0311489 A1 | 12/2011 | Deisseroth et al. | |
| 2011/0318775 A1 | 12/2011 | Mercola et al. | |
| 2012/0035583 A1* | 2/2012 | Sepkuty | A61B 5/4094 604/503 |
| 2012/0035725 A1 | 2/2012 | Gefen et al. | |
| 2012/0035726 A1 | 2/2012 | Gross et al. | |
| 2012/0101356 A1* | 4/2012 | Kim | A61B 5/04842 600/378 |
| 2012/0130302 A1 | 5/2012 | Wrobel et al. | |
| 2012/0149052 A1 | 6/2012 | Grohovaz et al. | |
| 2012/0172952 A1* | 7/2012 | Yoon | A61N 5/0622 607/92 |
| 2012/0287420 A1* | 11/2012 | McLaughlin | A61B 5/0084 356/72 |
| 2013/0030274 A1* | 1/2013 | Jamieson | A61B 5/6848 600/377 |
| 2013/0030275 A1 | 1/2013 | Seymour et al. | |
| 2013/0030353 A1 | 1/2013 | Seymour et al. | |
| 2013/0079615 A1* | 3/2013 | Yoon | A61B 5/04001 600/377 |
| 2013/0172712 A1* | 7/2013 | Koyrakh | A61B 5/0538 600/373 |
| 2014/0243640 A1* | 8/2014 | O'Dea | A61B 5/0084 600/373 |

FOREIGN PATENT DOCUMENTS

| | | |
|---|---|---|
| WO | 2009/124220 | 8/2009 |
| WO | 2009/131837 | 10/2009 |
| WO | 2010/029297 | 3/2010 |
| WO | 2010/056970 | 5/2010 |
| WO | 2010/105728 | 9/2010 |
| WO | 2011/057137 | 5/2011 |
| WO | 2011/057276 | 5/2011 |
| WO | 2011/116238 | 9/2011 |
| WO | 2012/052727 | 4/2012 |
| WO | 2012/061676 | 5/2012 |
| WO | 2012/061679 | 5/2012 |
| WO | 2012/061688 | 5/2012 |
| WO | 2012/061744 | 5/2012 |
| WO | 2012/075337 | 6/2012 |
| WO | 2013016389 | 1/2013 |
| WO | 2013016391 | 1/2013 |
| WO | 2013016392 | 1/2013 |

OTHER PUBLICATIONS

Dias et al., "New dry electrodes based on iridium oxide (IrO) for non-invasive biopotential recordings and stimulation," Sensors and Actuators A: Physical, 2010, vol. 164, pp. 28-34.

Farah et al., "Patterned Optical Activation of Retinal Ganglion Cells," Proceedings of the 29th Annual International Conference of the IEEE EMBS, Cite Internationale, Lyon, France, Aug. 23-26, 2007, pp. 6368-6370.

Froehlich et al., "Messung Und Analyse Monophasischer Aktionspotentiale Mit Hilfe Fraktal Beschichteter Elektroden—Teil I," Biomedizinsche Technik, Fachverlad Schiele Und Schoen GmbH, Berlin, DE, vol. 40, No. 6, Jun. 1, 1995, pp. 154-159.

Light-Induced Artifact, Retrieved from the Internet on Jun. 21, 2012 <URL: http://www.openoptogenetics.org/index.php?title=Light-Induced_Artifact>.

Lu Y et al: "Electrodeposited polypyrrolejcarbon nanotubes composite films electrodes for neural interfaces", Biomaterials, Elsevier Science Publishers BV., Barking, GB, vol. 31, No. 19, Jul. 1, 2010, pp. 5169-5181.

Pachnis, Neutralisation of myoelectric interference from recorded nerve signals using models of the electrode impedance, University College London Department of Electronic and Electrical Engineering, Sep. 2010.

PCT/US2012/048073 International Search Report and Written Opinion dated Oct. 17, 2012 (11 pages).

PCT/US2012/048075 International Search Report and Written Opinion dated Nov. 21, 2012 (17 pages).

PCT/US2012/048076 International Search Report and Written Opinion dated Oct. 17, 2012 (8 pages).

Shimada, "Neural Function Observation with Microelectrode Array," NIT Technical Review, Aug. 2009, vol. 7, No. 8, pp. 1-5.

Villalobos et al., "All-optical control of neuronal function via optical delivery of light-sensitive proteins and optogenetic stimulation," 2012 BiOs, SPRI Photonics West, 8207G-178, Session 7, p. 65.

Zhang et al., "A Microelectrode Array Incorporating an Optical Waveguide Device for Stimulation and Spatiotemporal Electrical Recording of Neural Activity," 31st Annual International Conference of the IEEE EMBS, Minneapolis, Minnesota, USA, Sep. 2-6, 2009, pp. 2046-2049.

Zhang et al., "Integrated device for optical stimulation and spatiotemporal electrical recording of neural activity in light-sensitized brain tissue," J Neural Eng, Oct. 2009, vol. 6(5), pp. 1-24.

Adamantidis et al., "Neural substrates of awakening probed with optogenetic control of hypocretin neurons," Nature, Nov. 2007, vol. 450, pp. 420-425.

Aravanis et al., "An optical neural interface: in vivo control of rodent motor cortex with integrated fiberoptic and optogenetic technology," Journal of Neural Engineering, 2007, vol. 4, pp. S143-S156.

Arenkiel et al., "In Vivo Light-Induced Activation of Neural Circuitry in Transgenic Mice Expressing Channelrhodopsin-2," Neuron, Apr. 2007, vol. 54, pp. 205-218.

(56) References Cited

OTHER PUBLICATIONS

Gradinaru et al., "Targeting and Readout Strategies for Fast Optical Neural Control In Vitro and In Vivo," The Journal of Neuroscience, Dec. 2007, vol. 27(52), pp. 14231-14238.

Zhang et al., "Channelrhodopsin-2 and optical control of excitable cells," Nature Methods, Oct. 2006, vol. 3, No. 10, pp. 785-792.

Zhang et al., "Multimodal fast optical interrogation of neural circuitry," Nature, Apr. 2007, vol. 446, pp. 633-641.

Zhang et al., "Circuit-breakers: optical technologies for probing neural signals and systems," Neuroscience, Aug. 20007, vol. 8, pp. 577-581.

Bernstein et al., "Prosthetic systems for therapeutic optical activation and silencing of genetically-targeted neurons," Proc Soc Photo Opt Instrum Eng, 2008, 6854, 68540H.

Royer et al., "Light activation and detection of hippocampal neurons in the behaving rat," Presentation Abstract, Neuroscience, Nov. 17, 2008.

\* cited by examiner

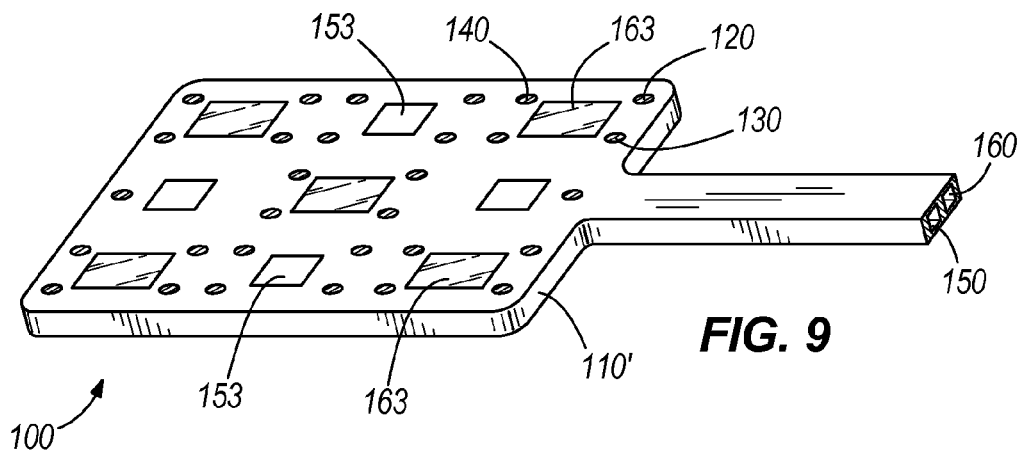
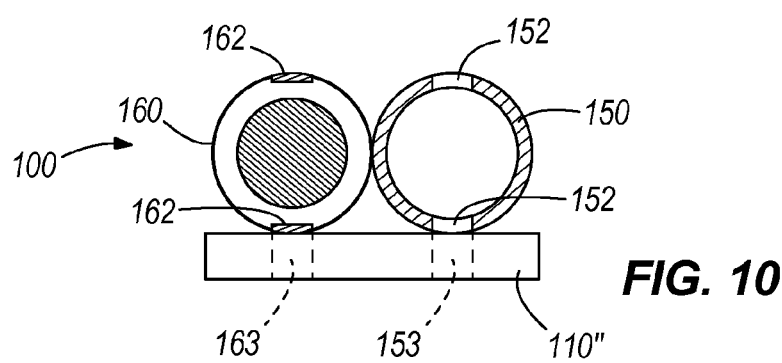
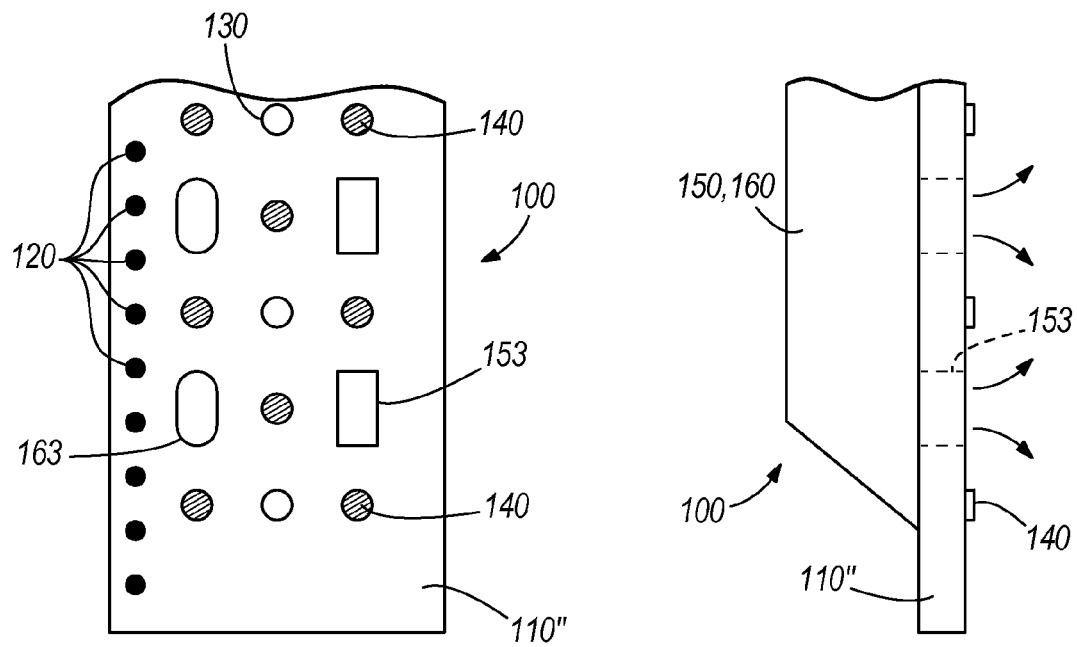
FIG. 9
FIG. 10
FIG. 11
FIG. 12

NEUROMODULATION TRANSFECTION SYSTEM WITH ACTIVE FLUID DELIVERY

CROSS-REFERENCE TO RELATED APPLICATIONS

This application claims the benefit of U.S. Provisional Application No. 61/511,371 filed Jul. 25, 2011, which is incorporated herein by reference in its entirety.

BACKGROUND

The present invention relates to the neural device field, and more specifically to a new and useful neuromodulation transfection system in the neural device field.

Various research and clinical neuroscience applications may involve a combination of different techniques for perturbing neural circuits and measuring the circuit's response. Stimulation may be electrical such as with conductive electrode sites, or may be optical such as with optogenetic tools. Such neurostimulation is typically sensed and/or recorded with electrical neurosensing. In particular, optogenetics is a developing technique that uses light-sensitive ion channels for optical stimulation of neural tissue, which allows experimenters or medical practitioners to selectively excite and/or silence particular neural channels with high precision. To create such light sensitive ion channels, the user performs a surgery in which an opsin such as ChR2 or Halorhodospin (e.g. delivered in the form of a protein or as a nucleotide for example using a viral vector) is introduced into target tissue, generally with cell-type specificity.

To optically stimulate or inhibit the neurons containing light-sensitive ion channels, an additional surgery is required to introduce an optical stimulator, electrical stimulator, and/or neurosensing components. In other words, the combined use of all these conventional neuroscience techniques requires multiple separate surgeries and/or implants, and every additional procedure or implant increases the difficulty of spatially co-locating the biologic agents, optical light source, neurosensing components, and other components such as drug delivery devices for therapeutic agents. Furthermore, performing multiple surgical procedures may risk creating complications for a patient or other subject.

Thus, there is a need in the neural device field to create a new and useful neuromodulation transfection system.

SUMMARY

In one embodiment, the invention provides a neural interface array including an optical waveguide, a thin film electrode array associated with the optical waveguide, the thin film electrode array having a plurality of electrodes, and a fluid delivery channel attached to at least one of the optical waveguide and the thin film electrode array.

In another embodiment, the invention provides a method for optical stimulation using an implanted neural interface array. The method includes steps of providing a neural interface array at an implantation site in a subject, the neural interface array having an optical waveguide, a thin film electrode array associated with the optical waveguide, the electrode array including a plurality of electrodes and a fluid delivery channel associated with the optical waveguide; delivering fluid to the implantation site using the fluid delivery channel; optically stimulating using the optical waveguide; and sensing an electrical signal using one of the plurality of electrodes.

In yet another embodiment, the invention provides a neural interface system with active fluid delivery. The system includes a neural interface array including an optical waveguide, a thin film electrode array associated with the optical waveguide, the electrode array comprising a plurality of electrodes, and a fluid delivery channel attached to the optical waveguide. The system also includes an electrical subsystem in communication with the electrode array; an optical subsystem in communication with the optical waveguide; and a fluidic subsystem in communication with the fluid delivery channel.

Other aspects of the invention will become apparent by consideration of the detailed description and accompanying drawings.

BRIEF DESCRIPTION OF THE DRAWINGS

FIG. 9 is a schematic of another embodiment of a neuromodulation transfection system; and FIG. 10 is a cross-sectional view of another embodiment of a neuromodulation transfection system;

FIG. 11 is a front view of another embodiment of a neuromodulation transfection system;

FIG. 12 is a side view of another embodiment of a neuromodulation transfection system.

DETAILED DESCRIPTION

Before embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
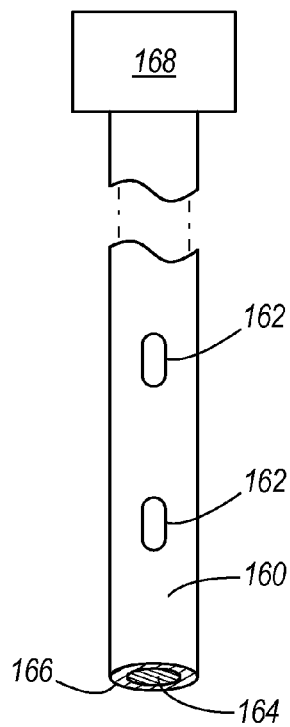
FIG. 1 shows a perspective view of an embodiment of a waveguide of a neuromodulation transfection system.
Figure 2:
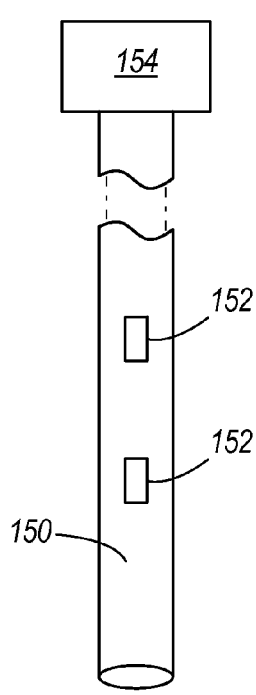
FIG. 2 shows a perspective view of an embodiment of a fluidic channel of a neuromodulation transfection system.
Figure 3:
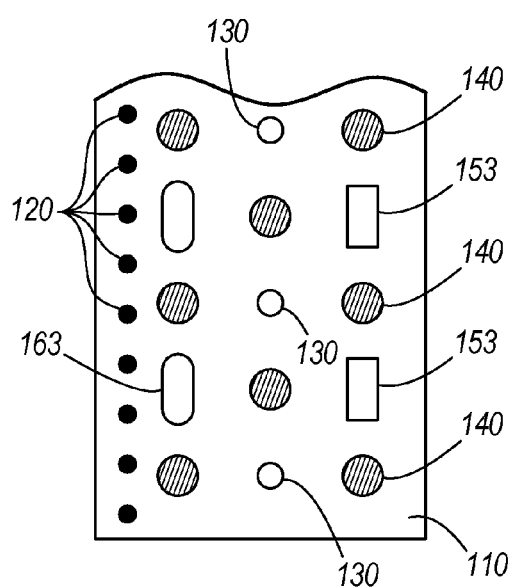
FIG. 3 shows diagram of an embodiment of a neural interface array of a neuromodulation transfection system.
Figure 4:
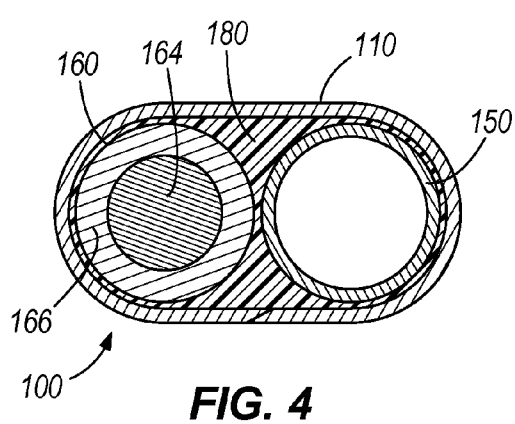
FIG. 4 is a cross-sectional view of an embodiment of a neuromodulation transfection system.
Figure 5:
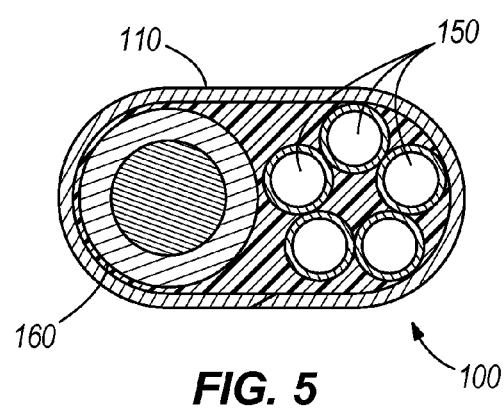
FIG. 5 is a cross-sectional view of another embodiment of a neuromodulation transfection system.

As shown in FIGS. 1-3, components of a neuromodulation transfection system 100 according to various embodiments include a waveguide 160 (FIG. 1), a fluidic channel 150 (FIG. 2), and a neural interface array 110, which can be combined a multiple ways to produce embodiments of the neuromodulation transfection system 100, for example as shown in FIGS. 4 and 5. The neural interface array 110, which can be inserted in or around tissue, includes one or more electrodes including a neurosensing electrode 120, a neurostimulation electrode 130, and/or an electroporation electrode 140. The fluidic channel 150 can be coupled to the neural interface array 110 and configured to deliver a biologic agent to target tissue. The waveguide 160 can be coupled to an optical light source and the neural interface array 110 and configured to optically stimulate selected tissue. Additionally, each of electrodes may be used for multiple purposes, including neurosensing, neurostimulation, and electroporation. Sensing and stimulating electrodes may in some embodiments have similar properties, but in other embodiments properties may differ depending on design requirements. Sensing electrodes with a small geometric area are generally suitable for small spatial volume sensing, whereas sensing electrodes having a larger geometric area are suitable for large volume (beyond the single cellular domain) sensing and lower power consumption during stimulation.

Electroporation (also known as electropermeabilization), in which an externally applied electric field increases the permeability of a cell membrane, may be performed to facilitate delivery of a vector into cells and subsequent expression of light-sensitive ion channels. Thus, in those embodiments in which the neural interface array 110 includes electroporation electrodes 140, the electroporation electrodes 140 may be used to facilitate introduction of a vector into neurons.

The neuromodulation transfection system 100 is multi-functional in that it can deliver biologic agents such as light-sensitive opsins and/or therapeutic or other bioactive agents to a targeted tissue region, selectively create electric fields to achieve effective electroporation in the targeted tissue region, selectively optically stimulate particular regions in the targeted tissue region, and sense neural activity in the targeted tissue region. The neuromodulation transfection system 100 may be implanted in a particular tissue location in a single surgical procedure, which ensures accurate spatial co-localization of the biologic agents using the fluidic channel 150, the waveguide 160 for optical stimulation, the neurosensing electrodes 120, neurostimulation electrodes 130, electroporation electrodes 140, and reduces the number of separate surgeries and implants that must be endured by the patient or other subject. In some embodiments, the neuromodulation transfection system 100 is implantable in brain tissue or over a surface in the brain or other neural surface (e.g. spinal cord or peripheral nerves), but may alternatively be implantable in or wrapped around other suitable tissue (e.g. muscle or heart). Implantation of the neuromodulation transfection system may in various embodiments be partial or complete; in either case, implantation is performed in a manner that provides access for delivery of fluids as well as electrical and optical communications as needed. In some embodiments the neuromodulation transfection system can be a completely implanted and self contained unit.

The neural interface array 110 functions to provide a medium for interaction with surrounding tissue. As noted above, the neural interface array 110 includes a plurality of electrodes, which includes an array of neurosensing electrodes 120 for recording electrical signals, and/or an array of electroporation electrodes 140 that emit an electrical field to stimulate electroporation of targeted cells. The neural interface array 110 may further include an array of neurostimulation electrodes 130 that electrically stimulate selected tissue regions, such as to elicit neural signals. Within each electrode array, the electrode sites may be individually and independently controllable, but at least a portion may alternatively be functionally grouped together, such as to form a selectively-controllable composite macroelectrode from a group of individual microelectrodes. The electroporation electrodes 140 may be selectively operated in a pattern to create an electrical field that induces molecular movement and/or electropermeabilization along a desired pathway in a targeted region of tissue. In particular, the electroporation electrodes 140 may be coupled to an external voltage driver that controls the electric field emitted by the electroporation electrodes 140.

In a first variation, the neural interface array 110 may be wrapped around an elongated carrier, such as a cylindrical or elliptical carrier as shown in US 2011/0093052 (hereinafter referred to as the '052 publication), which is incorporated in its entirety by this reference. In a second variation, the neural interface array 110 may be configured to wrap around tissue, such as the spinal cord. In these variations, some or all of the electrode sites may be ring electrodes, or circular or elliptical electrode sites distributed longitudinally along and/or circumferentially around the carrier. In a third variation, the neural interface array is planar (e.g. coupled to a planar carrier or formed as a sheet) and the electrode sites may be distributed along a face and/or edge of the probe, depending on the particular application of the system, as shown in U.S. Patent Application number 2011/0112591 (hereinafter referred to as the '591 publication), which is incorporated in its entirety by this reference. However, the electrode sites may be distributed on the neural interface array 110 in other suitable arrangements. In each of these variations, the carrier and/or neural interface array 110 itself may define a sharpened distal point to aid insertion into tissue (see, e.g., FIG. 7).

As shown in FIG. 3, the neural interface array 110 may further define a plurality of apertures that may be one or more variations. In one embodiment, a fluidic aperture 152 functions as a fluid delivery port that allows passage of fluid from the fluidic channel 150 which is coupled to the neural interface array 110. In another embodiment, an optical aperture 162 is a hole or window of optically diffusive material that functions as an optical port that allows passage of optical light from an optical light source or waveguide 160 coupled adjacent to (e.g. layered behind) the neural interface array 110. The optical port may be accompanied with light-directing elements that direct light from the optical light source or waveguide 160, such as the ports and light-directing elements described in the '591 publication. In either of these embodiments, the fluidic aperture 152 may include microvalves or other gating mechanisms to help regulate the passage of fluid through the fluid delivery port. Similarly, the optical aperture 162 may include micromirrors or other reflective or scattering mechanisms to help regulate the passage of light through the optical delivery port.

In some embodiments the neural interface array 110 is flexible, but in other embodiments may alternatively be rigid or semi-rigid. The neural interface array 110 in various embodiments is a thin-film array fabricated on a wafer, a glass substrate as large as the device, or on a large rolled polymer. Common thin-film techniques, such as used in semiconductor, microelectromechanical system (MEMS), flat panel technology, or roll-to-roll manufacturing may be used to create the neural interface array with standard deposition, photolithography, laser ablation, and etching techniques. Common substrate materials include SU-8, polyimide, parylene, silicone, etc. and/or other suitable materials. In particular, the neural interface array 110 may be formed by micromachining and/or other microfabrication techniques, such as semiconductor manufacturing processes that are known and readily understood by one ordinarily skilled in the art. In one embodiment, a thin-film neural interface array 110 includes a plurality of conductive layers deposited on a substrate and patterned to form the neurosensing electrodes 120, neurostimulation electrodes 130, and/or electroporation electrodes 140, using materials such as gold, platinum, iridium, titanium nitride, PEDOT, or other suitable conductive materials. The conductive layers may be additionally protected from the in vivo environment by the deposition and patterning of thin layer(s) of dielectric materials such as silicon carbide, silicon dioxide, and/or diamond at appropriate temperatures. Furthermore, the apertures (where an aperture may also be called a via) functioning as optical or fluidic ports may be formed through patterned etching or other suitable microfabrication processes. In various embodiments, a thin-film neural interface array 110 may further include insulating layers and conductive traces or interconnects that couple to the electrode sites and transmit signals to and from external instrumentation and the electrode sites, as disclosed in the '052 publication. However, the specific structure and formation of the electrode sites may depend on the particular application to which the neuromodulation transfection system 100 is applied. By having components made using thin-film or MEMS methods, one can readily combine the optical, fluidic, and electrical components of the neuromodulation transfection system for various applications and various subject anatomy by changing as few as one photolithographic step in the entire manufacturing process.

The fluidic channel 150 of the neuromodulation transfection system 100 functions to deliver a biologic agent or bioactive agent to target tissue, and may further function as a carrier that provides structural support for the system. The fluidic channel 150 in some embodiments is coupled to a fluid reservoir 154, such as a pump or other source, internal or external to the body, for active release into tissue. In various embodiments, the fluid delivered by the fluidic channel 150 can contain a biologic or bioactive agent such as light-sensitive opsins (either as proteins or nucleotides encoding for the proteins, which may be packaged into vectors), drugs or other therapeutic bioactive agents, and/or other suitable fluid or other substance. As noted above, cooperation between the fluidic channel 150 and the electroporation electrodes 140 facilitates transfection of neurons or other cells in order to introduce nucleic acids into the selected cells to enable the use of optogenetic techniques.

In various embodiments, the system 100 may include a single fluidic channel 150 for delivery of multiple kinds of agents, or may include multiple fluidic channels 150 (FIG. 5), for example to provide a distinct fluidic channel 150 for each of multiple kinds of biologic or bioactive agent. The fluidic channel 150 in some embodiments is coupled to the neural interface array 110, such as a separate structure fastened to the neural interface array 110 or a channel defined by the neural interface array 110. The fluidic channel 150 may be implemented using tubing made of a biocompatible metal and/or polymer, or other suitable material. As shown in FIG. 2, the fluidic channel 150 may define one or more fluidic apertures 152 through which the carried fluid is delivered to surrounding target tissue, although in some embodiments the fluid may additionally and/or alternatively exit the fluidic channel 150 at the distal end of the lumen of the channel 150. The fluidic apertures 152 may be specifically designed for particular types or regions of tissue, such as regions of the brain, spinal cord, peripheral nerves, or muscle. The fluidic apertures 152 of the fluidic channel 150 may be aligned with fluidic ports 153 on the neural interface array 110. The fluidic ports 153 of the neural interface array 110 and the fluidic apertures on the fluidic channel 150 may include microvalves or other gating mechanisms to help regulate the passage of fluid along the fluidic channel 150 and/or through the fluidic apertures 152.

The waveguide 160 of the neuromodulation transfection system 100 functions to optically stimulate selected tissue. The waveguide 160 is coupled to an optical light source 168 such as a light-emitting diode (LED), a laser diode, or other suitable laser or light source, such that the waveguide 160 carries and/or redirects light from the optical light source. For example, the waveguide 160 may be coupled to an external optical light source located outside the body. In some embodiments, localized light sources 168 (e.g. LEDs) may be integrated into the neural interface array 110 in place of using a waveguide 160 to direct light from another location. The optical light source may have selectively adjustable parameters, such as duration, intensity, and wavelength. The waveguide 160 may further function as a carrier or other structure for providing support for the system 100. As shown in FIG. 1, the waveguide 160 in one embodiment is an optical fiber, which may be a commercially-available optical fiber or an optical fiber that is customized to be specific to a particular application (e.g. use in a brain region). Alternatively, the waveguide 160 may include other suitable optical waveguide materials. For example, the waveguide 160 may be a thin-film structure made of a light-propagating material such as silicon oxynitride (Si-$O_xN_y$), $SiO_2$, silica, $S_3N_4$, SU-8, Cytop, or other suitable material, formed by one or more of several suitable fabrication processes including: micro-optoelectro-mechanical systems (MOEMS), photolithography, microembossing, thermal nanoimprint lithography (NIL), combined nanoimprinting and photolithography (CNP), and/or other suitable fabrication process. The waveguide 160 may include a refractor, reflector, lens, scattering element, or other light-directing elements that direct light from the optical light source. Other variations of the waveguide 160 may be similar to that described in the '591 publication, but may be other suitable kinds of optical light propagators. For example, the waveguide 160 may include an inner core 164 and a cladding layer 166 over the core 164, such that the core 164 and cladding layer 166 facilitate internal reflection along the waveguide 160. The cladding layer 166 may be etched to include one or more apertures 162 or diffusion ports through which the carried light from the optical light source may pass. The apertures 162 or diffusion ports of the waveguide 160 may be aligned with optical ports 163 of the neural interface array 110.

In one embodiment of the system, as shown in FIG. 4, the system 100 includes an elongated probe in which the neural interface array 110 is wrapped at least partially around the fluidic channel 150 and/or waveguide 160, which function as a carrier that provides structural support for the system 100. As noted above, the fluidic channel 150 and/or waveguide 160 may include a sharpened distal point to aid insertion of the system 100 into tissue. Further, the neural interface array 110 may include fluid delivery and/or optical ports that align with apertures of the fluidic channel and/or diffusion ports of the waveguide 160 to allow fluid and optical light pass through the array to surrounding selected tissues. At least some of the electroporation 140, neurostimulation 130, and/or neurosensing 120 electrodes are in various embodiments proximate to the apertures of the neural interface array 110, such that some electrodes are approximately co-located with the apertures to interact with the same region of tissue. In particular, the neurosensing electrodes 120, neurostimulation electrodes 130, electroporation electrodes 140, emission locations of bioactive agents and/or optical stimulation are, in many embodiments, adjacent to one another such that the same tissue regions (targeted cells) may be electropermeabilized by the electroporation electrodes 140, receive bioactive agents, be optically stimulated through the optical ports, electrically stimulated by neurostimulation electrodes 130, and/or sensed by neurosensing electrodes 120 without requiring repositioning of the implanted system 100 or replacement of the implanted system 100 with another device. For example, the electroporation electrodes 140 may be interspersed with the fluidic delivery ports and optical ports of the neural interface array 110. In embodiments such as this, the neural interface array 110 may be coupled to the waveguide 160 and fluidic channel 150 by wrapping the thin-film neural interface array 110 around the waveguide 160 and fluidic channel 150, injecting a polymer 180 such as silicone to fill the spaces between the neural interface array 110, waveguide 160, and fluidic channel 150, and cured to seal the assembled neuromodulation transfection system 100 (FIGS. 4 and 5). However, the system 100 may be manufactured and assembled in other suitable ways.

Figure 6:
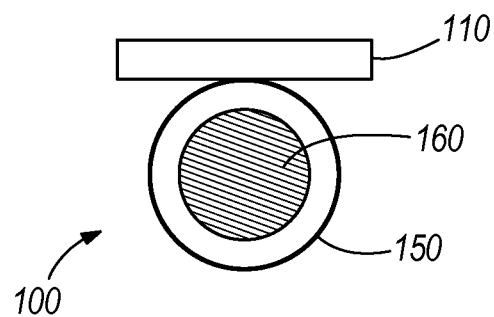
FIG. 6 is a cross-sectional view of another embodiment of a neuromodulation transfection system.
Figure 7:
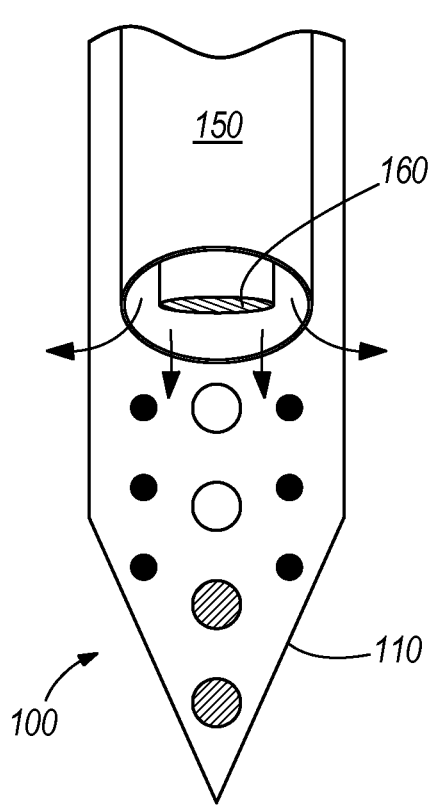
FIG. 7 is a perspective view of the neuromodulation transfection system of FIG. 6.
Figure 8:
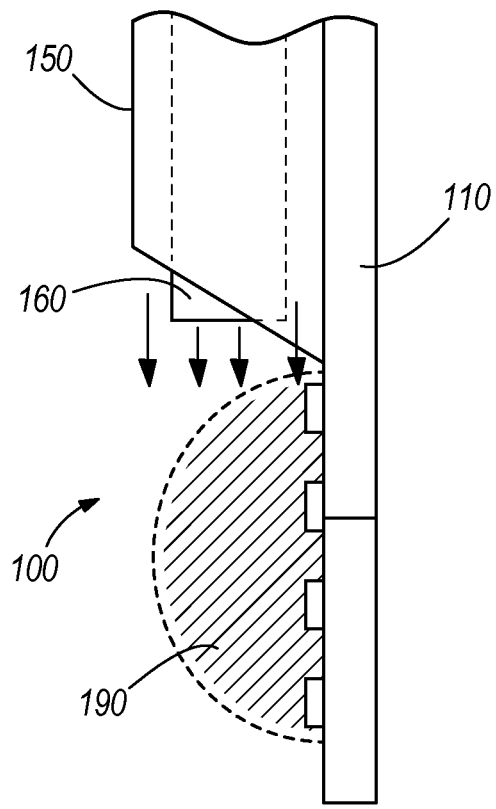
FIG. 8 is a side view of the neuromodulation transfection system of FIG. 6.

In another embodiment, as shown in FIGS. 6-8, the system 100 includes a planar probe 110 having a first side (which for convenience may be referred to as the "front" face) and a second side (which for convenience may be referred to as the "back" face). A carrier (such as the fluidic channel 150, waveguide 160 and/or other elongated structure) may be coupled to the front face or back face of the probe 110 for structure support. The fluidic channel 150 and waveguide may be concentrically or telescopically engaged, such as the waveguide 160 passing within the lumen of the fluidic channel 150 (e.g. as shown in FIGS. 6-8), thereby creating an annular space between the waveguide 160 and the wall of the fluidic channel 150 through which fluid may pass. Alternatively, the fluidic channel 150 and waveguide 160 may be adjacent to one another and longitudinally aligned with the probe 110", coupled to the front face and/or back face of the probe 110" (FIG. 10). The sites of the neurostimulation 120, neurosensing 130, and/or electroporation 140 electrodes may be arranged along the centerline or edge of one or both of the faces of the probe 110" (e.g. FIG. 11), but may be distributed in other suitable arrangements. As with other embodiments disclosed herein, the electrodes and locations of bioactive agents and/or optical simulation may be, in many embodiments, adjacent to one another such that they facilitate interaction with the same tissue regions. Thus, as shown in FIG. 8, delivery of light and fluid and electrical stimulation, sensing, and electroporation occur in approximately the same region 190 of tissue. The electroporation electrodes 140 may also be placed both near to and far from the fluidic port 152 and thereby be used to selectively transfect tissue in discrete anatomical locations without changing the position of the fluidic port itself. Creating discrete electroporation regions by controlling electrode placement allows specific neural circuits to be affected with a high degree of control. Identification of the neural circuits appropriate for electroporation may be performed using neurosensing electrodes 120 or using neurostimulation 130 or electroporation electrodes 140 in sensing mode.

In yet another embodiment, the system 100 may include a substantially planar neural interface array 110', such as for covering a tissue surface (e.g., brain or muscle). The substantially planar neural interface array 110' may additionally and/or alternatively be configured to wrap around tissue, such as the spinal cord. The fluidic channel 150 may be coupled to the surface of the substantially planar neural interface array 110', and/or be embedded within the substrate of the substantially planar neural interface array 110'. As shown in FIG. 9, in this embodiment the substantially planar neural interface array 110' includes distributed sites for neurosensing 120, neurostimulation 130, and/or electroporation 140 electrodes, and one or more optical ports 163 from which light emanates from one or more light sources (e.g., LEDs or light conducted through a waveguide 160). The substrate of the substantially planar neural interface array 110' may include one or more fluidic apertures 152 that allow for release of the bioactive agent from the system 100. As with other embodiments disclosed herein, the electrodes and locations of bioactive agents and/or optical stimulation may be adjacent to one another to facilitate interaction with the same tissue regions. For example, each type of electrode, optical light emission, and bioactive agent emission may be interspersed and distributed in an approximately regular pattern so that delivery of agents, cell transfection, light-based activation of ion channels, electrical stimulation, and electrical sensing may be performed in the same discrete location(s).

In additional embodiments, aspects of the various disclosed embodiments may be combined. For example, as shown in FIGS. 10-12, the system 100 may include a variant of the substantially planar neural interface array 110' probe disclosed above. In the neural interface array 110" of FIGS. 10-12, apertures pass between the back and front faces, with the electrode sites on the front face of the probe and the fluidic channel 150 and waveguide 160 coupled to the back face of the probe. In particular, the fluidic channel 150 and waveguide 160 may be longitudinally aligned with and adjacent to one another and with the probe such that at least some of the fluidic apertures 152 of the fluidic channel 150 and apertures 162 of the waveguide 160 are approximately aligned with the fluidic ports 153 and optical ports 163 of the probe to allow fluid and light to pass through the front side of the probe (FIG. 10). Some of the apertures 152, 162 of the fluidic channel 150 and waveguide 160 may face away from the probe such that fluid and light may pass into tissue in another direction, such as away from the front face of the probe (FIG. 10). In additional alternative embodiments, the system 100 may include the neural interface array 110", fluidic channel 150, optical source, and waveguide 160 coupled together in various suitable arrangements in which their relative positions enable approximate co-localization of their respective interactions with tissue. Further, in certain embodiments each of the neural interface array 110", fluidic channel 150, optical source, and waveguide 160 are modular and arrangeable in custom relative positions to suit particular applications.

Figure 13:
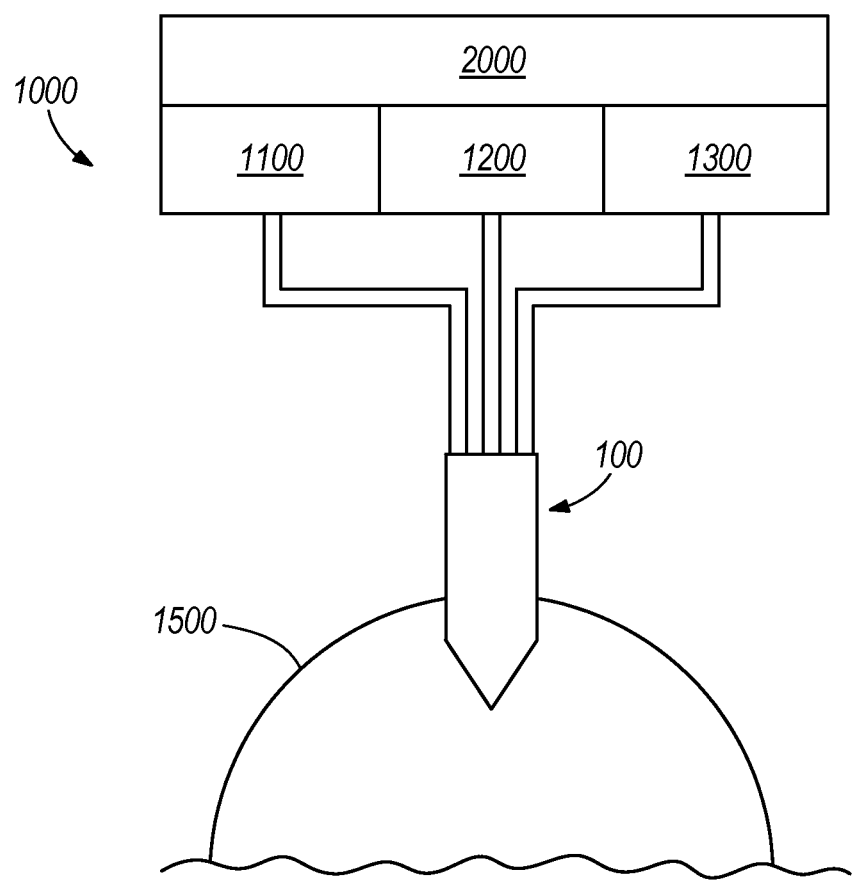
FIG. 13 shows an embodiment of a system for use with embodiments of the disclosed neuromodulation transfection system.

In certain embodiments the neuromodulation transfection system 100 is part of a neural interface system 1000, which may include an electrical subsystem 1100, an optical subsystem 1200, a fluidic subsystem 1300, and a controller 2000. The electrical subsystem 1100 functions to operate with the neural interface array 110, for example when the neuromodulation transfection system 100 is implanted into a subject 1500 (FIG. 13). The subject 1500 may include any number of animals into which the neuromodulation transfection system 100 may be implanted and with which the neural interface system 1000 may be employed, including without limitation rodents (e.g. rats, mice, rabbits, etc.) and primates (e.g. humans, monkeys, etc.).

The controller 2000 may control the electrical subsystem 1100, the optical subsystem 1200, and/or the fluidic subsystem 1300 to carry out the functions of the neural interface system 1000 such as those disclosed herein. The electrical subsystem 1100, optical subsystem 1200, fluidic subsystem 1300, and controller 2000 may be integrated into a single unit or may be separate units, and each may be external to the subject 1500 or may be part of an implanted device. Each of the electrical subsystem 1100, optical subsystem 1200, fluidic subsystem 1300, and controller 2000 may include a processor, memory, storage, input/output mechanisms, and communication mechanisms, including capabilities for wired and/or wireless communications within the components of the system 1000 and between the system 1000 and external computers and networks.

The electrical subsystem 1100 includes at least one of several variations of suitable electronic subsystems to operate with the neural interface array 110 or combinations thereof. The electrical subsystem 1100 may be a printed circuit board with or without onboard integrated circuits and/or on-chip circuitry for signal conditioning and/or stimulus generation, an Application Specific Integrated Circuit (ASIC), a multiplexer chip, a buffer amplifier, an electronics interface, a pulse generator (which produces signals such as a high-frequency, pulsed electric current, and which in certain embodiments may be implantable), a power supply (which in various embodiments can include an implantable rechargeable battery), integrated electronics for signal processing of the input (recorded) or output (stimulation) signals (either of which may be processed in real time), other suitable electrical subsystem, or combinations thereof, as disclosed in the '052 publication.

The optical subsystem 1200 includes power and control units to control the light source 168 in order to generate light pulses of suitable wavelength, duration, intensity, and pulse shape. The light source 168 (either directly or via the waveguide 160) functions to illuminate surrounding tissue and stimulating targeted tissue in a manner where the light is parallel, perpendicular, or at other angles relative to the electrodes.

The fluidic subsystem 1300 includes power and control units as well as provisions for storage (e.g. a tank, cartridge, or other reservoir) and delivery (e.g. one of a number of pumping mechanisms) of one or more fluids through one or multiple fluidic channels 150, including provisions for controlling the rate, volume, and timing of fluid delivery.

Thus, the invention provides, among other things, a neuromodulation transfection system and method. The present application discloses a neuromodulation transfection system that combines multiple functions such as those disclosed herein in a form that includes highly adaptable positioning of the various components to optimize the system performance in a specific subject or application. Various features and advantages of the invention are set forth in the following claims.

What is claimed is:

1. A neural interface array, comprising:
an optical waveguide having one or more optical apertures along its longitudinal axis;
a thin film electrode array comprising a plurality of electrodes, one or more optical ports, and one or more fluidic ports; and
a fluid delivery channel having one or more fluidic apertures along its longitudinal axis, wherein the optical waveguide, the fluid delivery channel, and the thin film electrode array are combined such that the one or more optical apertures are approximately aligned with the one or more optical ports, and the one or more fluidic apertures are approximately aligned with the one or more fluidic ports.

2. The neural interface array of claim 1, wherein the thin film electrode array comprises a flexible substrate which wraps around the optical waveguide and the fluid delivery channel.

3. The neural interface array of claim 1, wherein the optical waveguide and fluid delivery channel are concentric.

4. The neural interface array of claim 3, wherein the fluid delivery channel surrounds the optical waveguide.

5. The neural interface array of claim 1, wherein the fluid delivery channel has another fluidic aperture at its distal end.

6. The neural interface array of claim 5, wherein at least one of the plurality of electrodes comprises an electroporation electrode and wherein the electroporation electrode is adjacent to the another fluidic aperture.

7. The neural interface array of claim 1, wherein the plurality of electrodes comprises a neurosensing electrode.

8. The neural interface array of claim 1, wherein the plurality of electrodes comprises a neurostimulation electrode.

9. The neural interface array of claim 1, further comprising a plurality of fluid delivery channels combined with the optical waveguide and the thin film electrode array.

10. A method for optical stimulation using an implanted neural interface array, the neural interface array being located at an implantation site in a subject, the neural interface array including an optical waveguide having one or more optical apertures along its longitudinal axis, a thin film electrode array having a plurality of electrodes, one or more optical ports, and one or more fluidic ports, and a fluid delivery channel having one or more fluidic apertures along its longitudinal axis, wherein the one or more optical apertures are approximately aligned with the one or more optical ports, and the one or more fluidic apertures are approximately aligned with the one or more fluidic ports, the method comprising:
delivering fluid to the implantation site using the fluid delivery channel;
optically stimulating using the optical waveguide; and
sensing an electrical signal using one of the plurality of electrodes.

11. The method of claim 10, wherein the plurality of electrodes comprises at least one electroporation electrode, and wherein delivering fluid to the implantation site further comprises electroporating the implantation site.

12. The method of claim 10, wherein the fluid comprises a polynucleotide encoding for a light-sensitive ion channel.

13. The method of claim 10, wherein the neural interface array further comprises a plurality of fluid delivery channels.

14. The method of claim 10, wherein the implantation site comprises neural tissue.

15. The method of claim 10, wherein the plurality of electrodes further comprises a neurostimulation electrode and wherein the method further comprises electrically stimulating the implantation site using the neurostimulation electrode.

16. The method of claim 10, wherein the plurality of electrodes further comprises a plurality of electroporation electrodes, and wherein the method further comprises selectively activating the plurality of electroporation electrodes to electroporate only a subportion of the implantation site.

17. A neural interface system with active fluid delivery, comprising:
a neural interface array including:
an optical waveguide having one or more optical apertures on its sidewall,
a thin film electrode array comprising a plurality of electrodes, one or more optical ports, and one or more fluidic ports, and
a fluid delivery channel having one or more fluidic apertures on its sidewall, wherein the optical waveguide, the fluid delivery channel, and the thin film electrode array are assembled such that the one or more optical apertures are approximately aligned with the one or more optical ports, and the one or more fluidic apertures are approximately aligned with the one or more fluidic ports;
an electrical subsystem in communication with the thin film electrode array;
an optical subsystem in communication with the optical waveguide; and
a fluidic subsystem in communication with the fluid delivery channel.

18. The system of claim 17, wherein the thin film electrode array comprises a flexible substrate which wraps around the optical waveguide and the fluid delivery channel.

19. The system of claim 17, wherein the optical waveguide and fluid delivery channel are concentric.

20. The system of claim 19, wherein the fluid delivery channel surrounds the optical waveguide.

21. The system of claim 17, wherein the thin film electrode array comprises a flexible substrate and wherein the flexible substrate wraps around the optical waveguide and the fluid delivery channel.

22. The system of claim 21, wherein the neural interface array further including a plurality of fluid delivery channels which are wrapped around by the thin film electrode array.

23. The neural interface array of claim 1, wherein the thin film electrode array is substantially planar and the optical waveguide and the fluid delivery channel are embedded in the thin film electrode array.

24. The neural interface array of claim 1, wherein the thin film electrode array is substantially planar and the optical waveguide and the fluid delivery channel are disposed on an outer surface of the thin film electrode array.

* * * * *